(12) United States Patent
Bertling

(10) Patent No.: US 6,306,592 B1
(45) Date of Patent: *Oct. 23, 2001

(54) PROCESS FOR DETECTING AND QUANTIFYING NUCLEIC ACID MOLECULES

(75) Inventor: Wolf Bertling, Erlangen (DE)

(73) Assignee: november Aktiengesellschaft Gesellschaft fur Molekulare Medizin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,724
(22) PCT Filed: Jan. 7, 1997
(86) PCT No.: PCT/DE97/00008
§ 371 Date: Dec. 2, 1998
§ 102(e) Date: Dec. 2, 1998
(87) PCT Pub. No.: WO97/25441
PCT Pub. Date: Jul. 17, 1997

(30) Foreign Application Priority Data

Jan. 8, 1996 (DE) .............................................. 196 00 362

(51) Int. Cl.[7] .............................. C12Q 1/68; C12P 19/34; G01N 33/48; G01N 33/566; C07H 21/04
(52) U.S. Cl. .............................. 435/6; 435/7.1; 435/91.2; 435/91.1; 436/63; 436/94; 436/501; 536/23.1; 536/24.31; 536/24.32; 536/24.33; 210/656
(58) Field of Search .............................. 435/6, 7.1, 91.2, 435/91.1; 436/63, 94, 501; 536/24.3, 23.1, 24.31, 24.32, 24.33; 210/656

(56) References Cited

U.S. PATENT DOCUMENTS 4,794,075 * 12/1988 Ford et al. .............................. 435/6
5,217,863 * 6/1993 Cotton et al. .............................. 435/6
5,623,049 * 4/1997 Lobberding et al. ................. 530/300
5,795,976 * 8/1998 Oefner et al. ........................ 536/25.4
5,874,212 * 2/1999 Prockop et al. .......................... 435/6

FOREIGN PATENT DOCUMENTS

WO93/02216 * 2/1993 (WO) .
WO 95/06652 * 3/1995 (WO) .

OTHER PUBLICATIONS

Smooker et al Mutation Research vol. 288 pp. 65–77, 1993.*
Ganguly et al NAR vol. 18, No. 13 pp. 3933–3939, 1990.*
Babon et al NAR vol. 23, No. 24 pp. 5082–5084, 1995.*

* cited by examiner

Primary Examiner—Kenneth R. Horlick
Assistant Examiner—Jeffrey Siew
(74) Attorney, Agent, or Firm—Vanophem & Vanophem, P.C.

(57) ABSTRACT

The invention relates to a method of detecting and identifying nucleic aicd (NA) molecules within a population (I) of NA molecules of identical, similar or different sequence, in which: (a) the single-stranded or duplex ribonucleic acid (RNA) molecules or single-stranded deoxyribonucleic aicd (DNA) molecules contained in a population (I) iare convereted into a population (II) of duplex DNA molecules; b) the population (II) of duplex DNA molecules is subjected to denaturation and subsequent renaturation, so that a mixture of homo- and heteroduplex DNA molecules is present; c) heteroduplexes formed in the population (II) where unpaired of incorrectly paired nucleotides are present are reacted chemically with a carbodiimide compound; and d) the resulting carboddimide reactions products are characterized and quantified, characterized in that a chromatographic purification method is carried out between each of the steps a to d.

13 Claims, 1 Drawing Sheet

Microfiche Appendix Included
(1 Microfiche, 1 Pages)

PROCESS FOR DETECTING AND QUANTIFYING NUCLEIC ACID MOLECULES

FIELD OF THE INVENTION

The present invention relates to a method of identifying and quantifying nucleic acid molecules within a population of nucleic acid molecules of identical, similar, or different sequence, by chemically reacting unpaired or incorrectly paired nucleotides with a carbodiimide compound and forming heteroduplexes, which may then be quantified.

BACKGROUND OF THE INVENTION

An important field of molecular biology relates to the revealing of sequence variations in mixtures of largely homologous nucleic acids. The sequence comparison between DNA molecules for identifying variations not only adds to what is known about the molecular bases of phenotypic differences, for example hereditary diseases, but also permits continuous monitoring of NA populations, for example virus populations, during an infection. NA population is to be understood as meaning a plurality of NA molecules with an identical, the same or a different sequence. Furthermore, the sequence comparison also serves as a quality assurance characteristic when producing genetically engineered, bacterial or viral products or for detecting the occurrence of minute quantities of differing sequences in a population of homologous sequences.

The prior art knows several methods for tracking down sequence variations. Arguably the most laborious method is direct sequencing (Sanger F., Nicklen S., Coulson A. R., 1977, Proc. Natl. Acad. Sci. USA 74, 5463 et seq.; Maxam A. M., Gilbert W., 1977, Proc. Natl. Acad. Sci. USA 74, 560–564). This method does not allow a statistically significant number of individuals of an NA population to be tested for the occurrence of mutations. The application of indirect hybridization methods such as Southern (Southern E. M., 1975, J. Mol. Biol. 98, 503–517) or Northern (Alwine J. C., Kemp D. J., Stark G. R., 1977, Proc. Natl. Acad. Sci. USA 74, 5350–5354) only allow massive quantitative variations to be detected. Methods such as the ribonuclease protection assays (D. J. Freeman, A. S. Juan, 1981, J. Gen. Virol. 57, 103–117; E. Winter et al., 1985, PNAS 82, 7575–7579) for ribonucleic acid (RNA)-RNA heteroduplexes or for RNA-deoxyribonucleic acid (DNA) heteroduplexes (R. M. Myers et al., 1985, Science 230, 1242–1246) are slightly more sensitive.

Denaturing gradient gel electrophoresis (DGGE) has been made markedly more sensitive in recent years by employing "polymerase chain reaction"(PCR) technology and by using specific primers which facilitate separation in the gradient gel (V. C. Sheffield et al., 1992, Biofedback 12, 386–387). To separate the reaction products, even the differing sequences must be present in reasonable quantities. A further disadvantage of this method is the fact that, after separation and detection of a mutant, the site of the mutation cannot be specified, so that further identification reactions, for example sequencing, are subsequently required.

"Chemical cleavage reactions" using hydroxylamine and osmium tetroxide have the disadvantage that a large number of experimental manipulations with toxic chemicals and complex procedures are required (R. G. H. Cotton, 1989, Biochemistry 263, 1–10). In addition, they only work if substantial amounts of mutants are present. Finally, only certain mutations can be identified using this method.

A further prior-art method is based on the "single strand conformation polymorphism" (SSCP) reaction. Both this method and DGGE are carried out ((M Urita et al., 1989, PNAS 86, 2766–2770). A disadvantage of the SSCP reaction is that it leads to the identification of wrongly-positive samples. Moreover, this method fails in at least 10% of all cases if large amounts of mutant molecules are present.

Other prior-art methods only allow testing for the presence of a specific mutation, i.e. the verification of the presence, or absence, of an individual nucleotide (MAPREC: Chumakov K. M., Powers L. B., Noonan K. F., Roninson L. B., Levenbook I. S., 1991, Proc. Natl. Acad. Sci. USA 88, 199–203).

Methods in which carbodiimide is used have hitherto not proved popular in practice because this substance is difficult to handle and the methods lack sensitivity (D. F. Novack, 1986, Proc. Natl. Acad. Sci. USA, 83, 586 590; A. Ganguly, 1991, J. Biol. Chem. 266, 1235–1240; Offenlegungsschrift [Published Specification] DE 36 29 190 A1, A. Ganguly and D. J. Prockop, 1993, Nucl. Acids Res. 18 No. 13, 3933–3939).

A further method known from the prior art (WO 93/02216) is the method for detecting "mismatch" in heteroduplexes. A "mismatch-binding protein" is used, which is bound by first antibodies. These first antibodies, in turn, are recognized by second antibodies. Again, the method is complicated to carry out and can only be employed within limits.

In total, the lack of sensitivity relative to the minimum amount of mutants present within an NA population is the main disadvantage of the methods known from the prior art. Also, quantification of the NA molecules revealed is not possible. A further problem of the known methods is their unduly high failure rate.

It is an object of the present invention to provide a method, a device and a composition of means which overcome the disadvantages of the prior art.

SUMMARY OF THE INVENTION

Described is a method of detecting and quantifying nucleic acid (NA) molecules within a population (I) of NA molecules of identical, similar or different sequence, in which a) the single-stranded or duplex ribonucleic acid (RNA) molecules or single-stranded deoxyribonucleic acid (DNA) molecules contained in a population (I) are converted into a population (II) of duplex DNA molecules, b) the population (II) of duplex DNA molecules is subjected to denaturation and subsequent renaturation, so that a mixture of homo- and heteroduplex DNA molecules is present, c) heteroduplexes formed in the population (II) where unpaired or incorrectly paired nucleotides are present are reacted chemically with a carbodiimide compound, and d) the resulting carbodiimide reaction products are characterized and quantified, characterized in that a chromatographic purification method is carried out between each of the steps a to d.

DETAILED DESCRIPTION OF THE INVENTION

Figure 1:
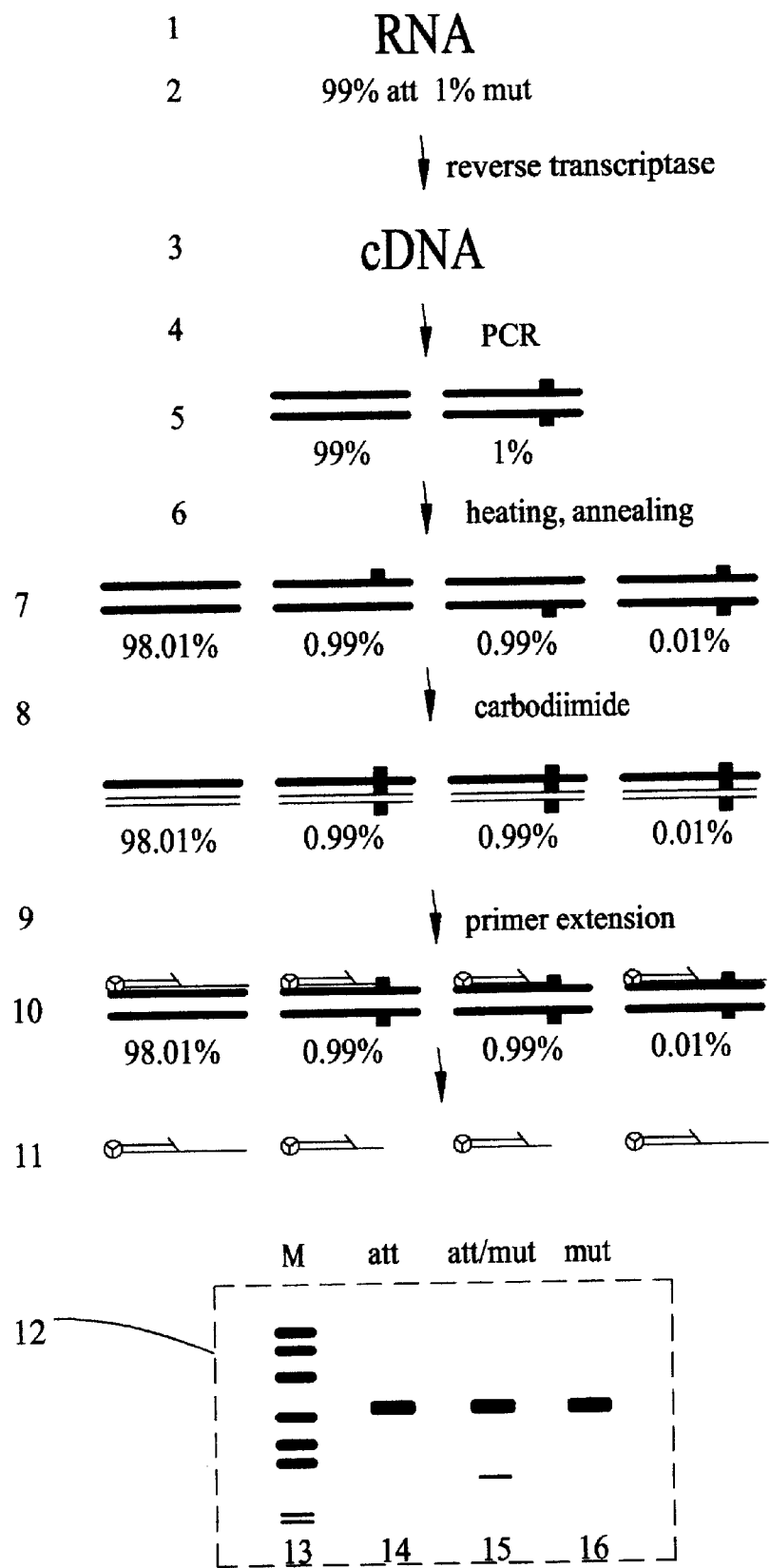
FIG. 1 is a flow chart detailing the method of revealing and quantifying nucleic acid molecules.

The present invention relates to a method of identifying and quantifying nucleic acid molecules within a population of nucleic acid molecules of identical, similar, or different sequence, by chemically reacting unpaired or incorrectly paired nucleotides with a carbodiimide compound and forming heteroduplexes, which may then be quantified.

The term "heteroduplex" as used herein is defined as double-stranded DNA molecule with at least one mismatch, i.e. one base-pair is incorrectly paired. A "homoduplex" as used herein is a double-stranded DNA molecule with no mismatches, i.e. all bases of the complementary strands are correctly paired.

As used herein, "nucleic-acid specific enzymes" are enzymes which bind or modify DNA. A "carbodiimide compound" is a compound of the general formula: $R_1$—N=C=N—$R_2$.

A "chromatographic purification method" is a method for separating substances, wherein one substance is retained at a solid phase and the other substance remains in a mobile phase.

As used herein, a "similar sequence" is a sequence which differs partly from another sequence. A "differing sequence" is a sequence which differs about the entire length from another sequence.

A "suitable primer" is a primer which binds under polymerase chain reaction (PCR) conditions at a defined position and acts as a polymerase-start position.

A "mismatch-detecting substance" is a substance which binds at a DNA at or nearby the position of the mismatch.

The advantage of the method according to the invention is that it can be applied in particular to unamplified genomic DNA. A further remarkable advantage is that the mutation within the fragment can be localized in a single reaction step. Also, small amounts of mutant nucleic acids can be detected in a population of homologous molecules. Up to a proportion of 50% mutants, this always leads to a multiplication of the molecules with differing sequences which are present within the population. Thus, the method according to the invention can be used, for example, for the secondary analysis of amplified DNA. This allows the detection of whether a revealed and identified sequence is typical of the existing NA population or whether it can be attributed to a contamination with similar DNA. It even allows the detection of contaminations on a molecular scale which, if PCR methods are applied, lead to a considerable distortion of the detection reactions. Thus, the method according to the invention makes possible drastically improved detection results, in particular in combination with PCR methods.

The mixture of homo- and heteroduplex DNA molecules can be reacted with the carbodiimide compound to give carbodiimide reaction products. Advantageously, it is provided that the mixture of homo- and heteroduplex DNA molecules is treated with NA-specific enzymes and cofactors to detect a lack of base pairing. A further especially advantageous embodiment of the method consists in the fact that the mixture of homo-and heteroduplex DNA molecules which has been reacted with the carbodiimide compound is subjected to an extension reaction, in particular a primer extension reaction, preferably after having been purified. The products of the extension reaction, finally, can be characterized and quantified. Here, customary, for example PCR, methods are employed.

The method according to the invention is especially accurate when the extension reaction is carried out repeatedly. The primer or the extension products are preferably labeled. It is considered especially advantageous to use labeled oligonucleotides. The oligonucleotides can be labeled in a separate step. This allows separation of the labels to be incorporated. The specificity of the method can be increased in particular by using oligonucleotides which have been selected for size and identity.

The method is especially sensitive when the purification step comprises a chromatographic purification method. The chromatographic purification method may be a column or batch method which is carried out using matrices such as silica gel or DEAE material, all of which allow a separation on the principle of ion exchange, affinity or size exclusion. The purification step may be carried out in particular using a silica column. The advantage here is that thermal destruction of carbodiimide residues and extraction and precipitation with ethanol, which are required in the prior art, can be dispensed with.

In accordance with the invention, there is furthermore provided a device and a composition of a plurality of means for carrying out the method.

Finally, the object according to the invention is achieved by the use of heteroduplexes for revealing and quantifying NA molecules within a population of NA molecules of identical, similar or differing sequence.

In the test which follows, carrying out the method according to the invention will first be illustrated in greater detail in general terms with reference to detecting mutations in NA populations.

Preparation of the heteroduplex for the reaction with carbodiimide comprises an amplification reaction with suitable primers and, in the case of RNA, previous generation of cDNA in a reverse transcription reaction. The reaction products may be detected via gels, preferably high-strength polyacrylamide gels, but also by other chromatographic methods, for example silica columns or silica gel columns, HPLC (high pressure liquid chromatography), or by means of antibodies.

Before or during the carbodiimide treatment, other additional "mismatch-detecting substances", such as, for example, the proteins Mut-L or Mut-S, can be employed in the method according to the invention for increasing the reactivity of the carbodiimide derivatives If reverse transcription and/or amplification of the individuals of the population has taken place, it is expedient to choose primers for the subsequent enzymatic reaction with DNA polymerase which are not outside the primers for amplification, or reverse transcription, respectively. If homodimers are analyzed subsequently to amplification (by means of PCR), the result is a primer extension product of defined length. The existence of a mutation causes formation of a heteroduplex, which leads to the formation of a carbodiimide-modified nucleotide at a particular location and causes replication of the chain to be terminated by the DNA polymerase. Depending on the location of the mutation, the result is a termination product of characteristic length, which can be identified in a subsequent analysis for its presence (for example antibodies against carbodiimide-modified nucleotides) or its length (by means of gel electrophoresis or chromatographic methods, for example HPLC).

Analysis of an RNA population can be described by an analytical scheme with the following steps:
 Using a suitable primer, a single-stranded or else duplex DNA is provided, prepared, obtained or otherwise acquired for the subsequent steps in a reverse transcription reaction. When preparing from RNA, it can be expedient to use an enzyme which is capable of operating at higher temperatures. In a subsequent step, duplex DNA is prepared, obtained or otherwise acquired from any existing single-stranded DNA with the aid of a suitable primer.

Duplex DNA molecules may, but need not be, subjected to an amplification reaction. This can be the reaction known as PCR, or a derivative thereof, for example polymerase chain ligation.

After concluding these preliminary tasks, duplex homodimeric DNA molecules are present. Even if an amplification has been carried out beforehand, the ratio of the homodimers still corresponds to the ratio of the individual sequence variants prevailing in the original population (I). The homodimeric duplexes are melted in a subsequent denaturation step, which is preferably carried out in a suitable solution by elevating the temperature. In a subsequent renaturation step, which is preferably triggered by reducing the temperature, the homologous single strands pair up statistically to give homo- and heteroduplexes. It must be taken into consideration that, the lower the number of individuals with varying sequences in the original population (I), the higher the probability that each of the mutant single strands leads to the formation of a heteroduplex. In the extreme case, the number of heteroduplexes formed is twice the number of the individuals which have had a differing sequence in the original population (I).

The next step is the reaction of the heteroduplex homodimeric mixtures with carbodiimide derivatives in the presence or absence of mutation-detecting proteins. When choosing suitable concentration and buffer conditions, no coupling of carbodiimide derivatives with homodimers takes place.

The nucleic acids and carbodiimide derivatives are then separated from the NA reaction products, preferably via a column, for example a silica gel column. The resulting purified reaction products, which may have been subjected to incipient concentration in further steps, are now available for use in a subsequent enzymatic reaction.

A DNA polymerase, which, using the primers bound to the nucleic acid templates, produces replicates of these templates, is added to the mixture in a suitable buffer medium with addition of nucleotides, which may be labeled as triphosphates, and suitable primers, which may be radiolabeled. The presence of a carbodiimide modification leads to chain elongation termination of the freshly replicated NA molecule and thus to the presence of a reaction product, preferably labeled, which has a length which is characteristic for the particular localization of the sequence variation. Increased sensitivity can be achieved by using radiolabeled oligonucleotides.

This replication product can be characterized in a subsequent reaction or sequence of reactions. The reaction batch is preferably applied to a high-strength polyacrylamide gel and separated, which permits length and quantity of the original and mutant NA population proportions to be determined simultaneously. However, the reaction product may also be separated and quantified by other chromatographic methods, for example the use of HPLC analysis. Under certain circumstances, it may also be meaningful to react the reaction product with antibodies which are specific for carbodiimide-modified nucleotides and to prepare them for further detection. While the binding of antibodies may primarily make determination of the size of the reaction product more difficult, it can nevertheless lead to an increase in sensitivity, specifically in connection with other antibody-specific antibodies.

Two use examples for carrying out the method according to the invention are described in the text which follows:

EXAMPLE 1

Reaction of Heteroduplexes with Carbodiimide a.) Generation of DNA Heteroduplexes:

Two nucleic acids which have the same length and whose sequence differs only at one position are used for a reaction batch. The sequence is the section of nucleotide No. 394 to nucleotide 572 of the attenuated poliomyelitis virus stereotype 3. The sequence variation between the two nucleic acids employed is in position 472. Approximately 99% if the NA population have thymin as base in this position, while 1% has a cytosine as base in this position, in each case on the coding strand. Both NA variants are in duplex form and are multiplied by a conventional amplification reaction viz. the PCR method described in EP-A-0200362. After the reaction, the aqeous phase of the PCR is mixed with five volumes of PB buffer and subsequently spun for 1 minute at 15000 rotations per minute (rpm) through a silica gel column. In the next step, the silica gel column is washed with 750 $\mu$m of guanidinium chloride solution (35 g per 100 ml of water) and recentrifuged for 1 minute at 15000 rpm. This removes the remaining primers and dimers from the silica gel column. 750 $\mu$l of PE washing buffer area subsequently applied to the silica gel column, and this is also spun for 1 minute. Residual washing buffer in the silica gel column is removed by recentrifuging for 1 minute. The silica gel column is then transferred into a 1.5 ml reaction vessel and the DNA bound to the silica gel column is eluted in 50 $\mu$l of water by applying and recentrifuging for 1 minute. the reaction, the aqueous phase of the PCR is mixed with five volumes of PB buffer and subsequently spun for 1 minute at 15000 rotations per minute (rpm) through a silica gel column. In the next step, the silica gel column is washed with 750 $\mu$l of guanidinium chloride solution (35 g per 100 ml of water) and recentrifuged for 1 minute at 15000 rpm. This removes the remaining primers and dimers from the silica gel column. 750 $\mu$l of PE washing buffer are subsequently applied to the silica gel column, and this is also spun for 1 minute. Residual washing buffer in the silica gel column is removed by recentrifuging for 1 minute. The silica gel column is then transferred into a 1.5 ml reaction vessel and the DNA bound to the silica gel column is eluted in 50 $\mu$l of water by applying and recentrifuging for 1 minute.

b) Carbodiimide Modification of the DNA Heteroduplexes:

20 $\mu$l of the elute are transferred into a silicon-treated "thin-walled tube ". The existing amount of DNA now varies between 40 and 500 ng. The amount is normally 200 ng per batch. After 10 $\mu$l of hybridization buffer (3M sodium chloride; 35 mM MgCl$_2$ in 30 mM Tris-HCl buffer, pH 7.4) and 70 $\mu$l of water have been added, the batch is overlaid with 2 drops of mineral oil and denatured for 10 minutes in water bath at 100° C and then immediately transferred onto ice. Annealing takes place overnight at 42° C. Five volumes of PB buffer (contains guanidinium hydrochloride) are then added, and the batch is mixed and spun for 1 minute. This is followed by repurification over the silica gel column. Elution is performed into 60 $\mu$l of TE (0.1 mM EDTA, 10 mM Tris-HCl, pH 7.4). A fresh, 200 mM carbodiimide solution (84.7 mg/ml) is made up immediately beforehand (CME carbodiimide: N-cyclohexyl-N-(2-morpholino-ethyl) carbodiimide methyl-p-toluenesulphonate). The carbodiimide solution is treated with the desired amount of heteroduplex DNA (200—200 ng), which has been formed by annealing. After 4 µl of 1M sodium borate solution, pH 8.0, have been added, 10 µl of the carbodiimide solution are added and the mixture is incubated for 3 hours at 30° C. The batch is subsequently made up to 40 µl water.

c. Removal of Unbound Carbodiimide from the Reaction mixture:

The carbodiimide modification batch is treated with five volumes of PB buffer, mixed and spun for 1 minute. This is followed by another column purification step, during which the washing procedure is repeated three times. The DNA is eluted from the silica gel column overnight at room temperature using 26 µl of TE (pH 7.4). The silica gel column is subsequently spun for 1 minute.

EXAMPLE 2

Carbodiimide-conjugate-specific Primer Extension:

A typical primer extension batch is composed of 5 µl of the heteroduplex DNA described in Example 1 and 5 µl of the PCR mixture which contains the nucleotides A, G and T in a concentration of 0.4 mM, the nucleotide C in a concentration of 20 µM and furthermore 100 µCi of $p^{32}$ dCTP. In addition to 100 pmol of the oligonucleotides required for primer extension and 5 units of Taq DNA polymerase, the 100-µl- batch additionally comprises buffer (10 mM Tris-HCl, pH 8.3, 3.5 mM $MgCl_2$; 75 mM KCl) and BSA at an end concentration of 7 µg/ml. Only when the temperature has risen to 90° C are the samples introduced into the Perkin Elmer Cycler 480. After one cycle has been performed, the reaction has ended. The samples are then stored on ice. The cycle consists of a denaturation (70 sec. at 96° C) followed by an annealing reaction (30 sec. at 62° C) and an extension (1 min. at 72° C). After the end of the reaction, 5 µl of loading buffer (50% sucrose, 0.1 M EDTA pH 8.0, 0.1% Bromophenol Blue, 0.1% xylene xylanol) are added and the batch is stored on ice. An 8-µl-aliquot is then applied to a 10% PAA gel. Detection can be affected by superimposing an X-ray film or by exposure in a phosphorus imager, which facilitates quantification.

The method described in the preceding examples is illustrated in the drawing in the form of a flow chart.

The original population chosen as example was an RnA population representing 99% of attenunated (att) and 1% of mutated (mut) RNA viruses (reference symbol 1). After reverse transcription 2, cNDA 3 is formed in the same proportion. In a further step, this cDNA is amplified by a PCR reaction 4 over 30 cycles. The ratio of attenuated to mutated amplification products is still 99:1% (reference symbol 5). In a last denaturation/renaturation step 6, during which DNA polymerase activity was excluded, homo- and heteroduplexes 7 are now present in new ratios. This mixture of homo- and heteroduplexes 7 is now reacted with carbodiimide 8 and, after purification, subjected to a primer extension reaction 9. The next step is the marker application 10. The labeled reaction products 11 are finally analyzed by gel electrophoresis 12. A diagran of the resulting pattern shows, besides a marker M, the analysis of a pure homo-duplex batch, a mixed hetero/homoduplex batch and a pure heteroduplex batch. The reference symbol 13 refers to the marker application, reference symbol 14 to a first control lane of 100% attenuated NA; the reference symbol 15 to application of the analysis of the analysis and reference symbol 16 to a second control lane of 100% mutated NA.

What is claimed is:

1. A method of detecting and quantifying nucleic acid molecules within a population I of nucleic acid molecules of identical, similar or different sequence, comprising a) converting single-stranded or duplex ribonucleic acid (RNA) molecules or single-stranded deoxyribonucleic acid (DNA) molecules contained in population I into a population II of duplex DNA molecules, b) denaturating and subsequently renaturating the population II of duplex DNA molecules thereby forming a mixture of homo-duplex and heteroduplex DNA molecules, c) reacting chemically with a carbodiimide compound the heteroduplexes formed in the population II where unpaired or incorrectly paired nucleotides are present, d) detecting and quantifying the resulting carbodiimide reaction products, and performing a chromatographic purification method between each of steps a to d.

2. The method of claim 1 wherein the chromatographic purification method utilized is a column or batch method utilizing silica gel.

3. The method of claim 1 wherein the purification step utilizes a silica column.

4. The method of claim 1 wherein the carbodiimide compound utilized is selected from the group consisting of N-cyclohexyl-N'-(2-morpholinoethyl) carbodiimide; dimethyl adipimidaaate; pyromellitic diimide; N,N'-bix(2,6-dimethylphenyl)perylene-3,4,9,-tetra carboxylic diimide; bis(trimethylsilyl) carbodiimide; N,N'-di-tertiary-butylcarbodiimide; N,N'-dicyclohexylcarbodiimide; N,N'-diisopropylcarbodiimide; N-3-dimethylaminopropyl)-N'-ethylcarbodiimide; N,N'-ditridecylperylene-3,4,9,10-tetracarboxylic diimide; dimethyl pimelimidate; dimethyl octanimidate; and 1-ethyl-3-(3-dimethylaminopropyl) carbodiimide.

5. The method of claim 1 further comprising treating the mixture of homoduplex and heteroduplex DNA molecules with nucleic acid-specific enzymes and cofactors.

6. The method of claim 1 further comprising adding during step c mismatch-recognizing proteins.

7. The method of claim 1 further comprising amplifying one or more times population II prior to step c.

8. The method of claim 4 further comprising in step d subjecting the mixture to an extension reaction and the extension products are detected and quantified.

9. The method of claim 8 wherein a primer is used for the extension reaction.

10. The method of claim 8 wherein a modified or unmodified oligonucleotide is used in the extension reaction.

11. The method of claim 9 wherein the primer or the extension product is labeled.

12. The method of claim 8 further comprising performing the extension reaction repeatedly.

13. The method of claim 1 wherein the carbodiimide reaction products are detected by means of carbodiimide-specific antibodies.

* * * * *

UNITED STATES PATENT AND TRADEMARK OFFICE
CERTIFICATE OF CORRECTION

PATENT NO.      : 6,306,592 B1                                            Page 1 of 1
DATED           : October 23, 2001
INVENTOR(S)     : Bertling It is certified that error appears in the above-identified patent and that said Letters Patent is hereby corrected as shown below:

Column 1,
Lines 1-3, please remove "PROCESS FOR DETECTING AND QUANTIFYING NUCLEIC ACID MOLECULES" and insert -- METHOD OF REVEALING AND QUANTIFYING NUCLEIC ACID MOLECULES --.

Column 4,
Line 40, after "derivatives" insert a period -- . --.

Column 6,
Line 14, after "99%" delete "if" insert -- of --.
Line 24, delete "750 um" and insert -- 750 ul --.
Line 27, delete "area" and insert -- are --.
Beginning at line 33 "the" and ending at line 47 ending at "minute", delete whole paragraph.
Line 55, after "in" insert -- a --.

Column 7,
Line 5, delete "c." and insert -- c.) --.
Line 6, delete "mixture" and insert -- Mixture --.
Line 17, delete "Primer Extension:" and insert -- primer extension: --.
Line 42, delete "RnA" and insert -- RNA --.
Line 50, delete "excluded." and insert -- excluded, --.

Column 8,
Line 2, after "analysis" delete "of the analysis".
Line 29, delete "adipimidaaate" and insert -- adipimidate --.

Signed and Sealed this

Twenty-fifth Day of February, 2003

JAMES E. ROGAN
*Director of the United States Patent and Trademark Office*